United States Patent [19]
Boubel et al.

[11] 3,965,748
[45] June 29, 1976

[54] APPARATUS FOR AUTOMATICALLY MEASURING PARTICULATE EMISSIONS IN GAS FLOW

[75] Inventors: Richard W. Boubel, Corvallis, Oreg.; David C. Babler, Brush Prairie; Donald W. Peter, Battleground, both of Wash.

[73] Assignee: Rader Companies, Inc., Portland, Oreg.

[22] Filed: Nov. 18, 1974

[21] Appl. No.: 524,749

[52] U.S. Cl. ............................ 73/421.5 A; 73/28
[51] Int. Cl.² ....................................... G01N 1/24
[58] Field of Search ........... 73/28, 421.5 A, 421.5 R

[56] References Cited
UNITED STATES PATENTS

| | | | |
|---|---|---|---|
| 2,982,131 | 5/1961 | Rosinski | 73/421.5 A |
| 3,784,902 | 1/1974 | Huber | 73/421.5 A |
| 3,841,145 | 10/1974 | Boubel | 73/28 |

*Primary Examiner*—James J. Gill
*Assistant Examiner*—Anthony V. Ciarlante
*Attorney, Agent, or Firm*—Klarquist, Sparkman, Campbell, Leigh, Hall & Whinston

[57] ABSTRACT

A stack sampler for collecting particulate samplings in gaseous emissions includes means for automatically matching the volume rate of flow through the sampler to the flow in the stack. Pressure drops and temperatures in the stack and in the sampler are continuously detected and applied to calculating circuitry which controls a valve in the sampler for maintaining isokinetic flow conditions. Filter means removably disposed in the sampler collects particulate material from the gaseous emission during the isokinetic flow which is obtained. Also, flow and flow rate are detected and displayed.

15 Claims, 7 Drawing Figures

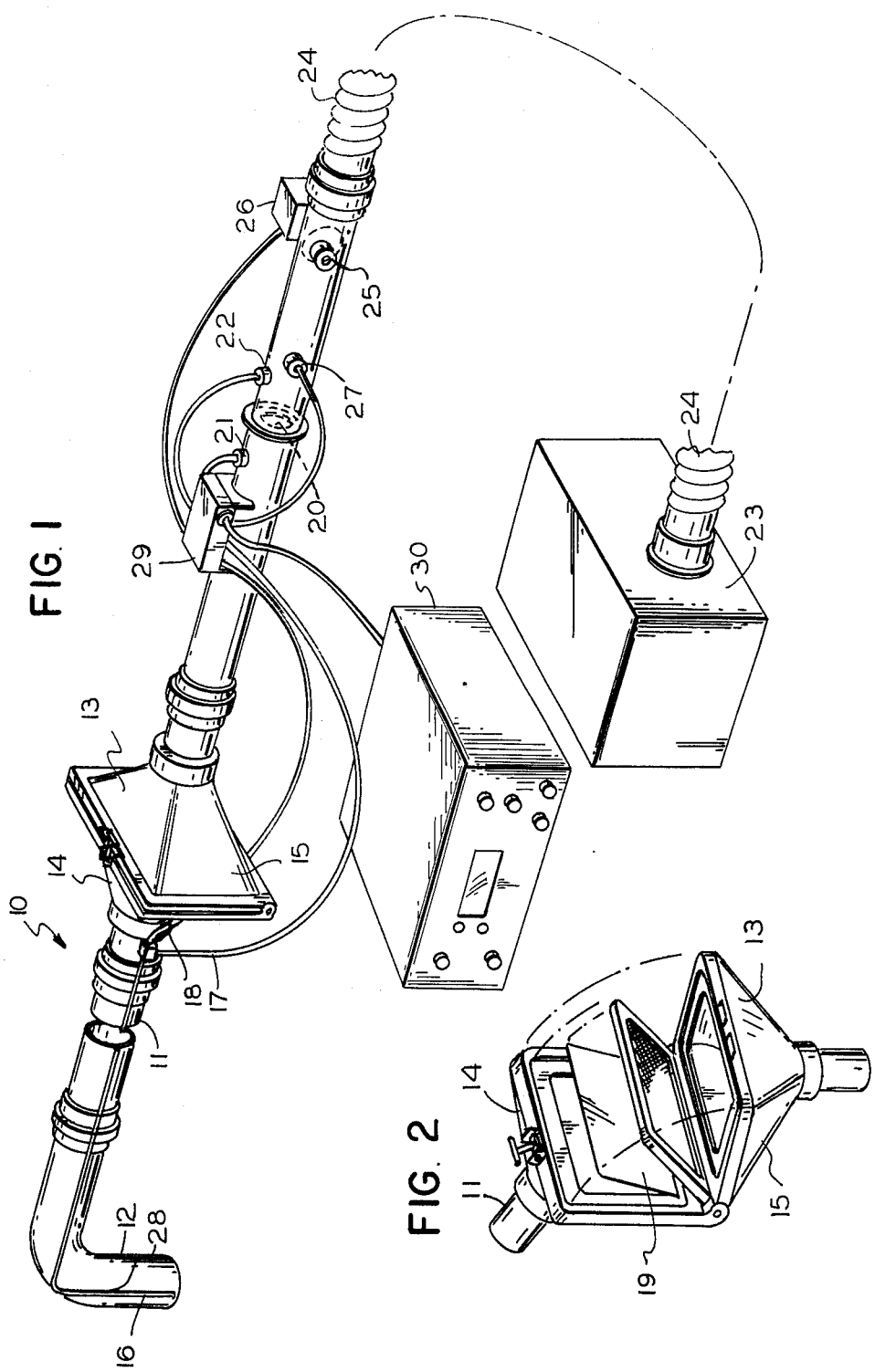

APPARATUS FOR AUTOMATICALLY MEASURING PARTICULATE EMISSIONS IN GAS FLOW

BACKGROUND OF THE INVENTION

This invention relates to apparatus for sampling the emissions in a gas flow and, more particularly, to apparatus adapted for isokinetic sampling of a gas flow.

Sampling apparatus heretofore available for measuring emissions, i.e., particulate matter, under isokinetic flow conditions has required considerable manual adjustment before a single reading in a stack or other conduit could be achieved. An apparatus of this type is shown in Boubel, patent application Ser. No. 385,310, filed Aug. 3, 1973, now U.S. Pat. No. 3,841,145. This sampler comprises a generally cylindrical tube and includes an inlet nozzle disposed at the forward end of the tube and adapted for insertion into a stack or like conduit through which a gas is flowing. A Pitot tube is attached to the nozzle and is adapted for insertion into the stack with the nozzle for measuring the velocity of gas flowing through the stack. A filter is disposed in the tube downstream of the nozzle for collecting particulate matter. The filter is disposed in a housing which comprises upstream and downstream sections removably connected together to facilitate rinsing of the sampler upstream of the filter as is necessary fully to account for particulate matter removed from the flow.

The sampler further comprises a suction blower which is connected to the downstream end of the tube. A flow measuring orifice is disposed in the tube between the filter and the blower and a control valve is provided for regulating the flow therethrough.

In using a sampler of this type to measure emissions in a stack or similar conduit, the temperature of the gas flowing through the stack is first measured and the inlet nozzle with the Pitot tube attached is inserted into the stack to measure the velocity pressure. Appropriate calibration curves are used to convert the reading on a velocity pressure gauge into a gas velocity or volume rate of flow through the stack.

The suction blower is then started and flow is drawn through the tube to determine the average sample temperature therein. Once the temperature is determined, other calibration curves are used to calculate the reading that should be obtained on a pressure gauge which measures the pressure drop across the orifice to determine the flow through the sampler that will achieve isokinetic conditions. The flow is then regulated by means of the control valve such that the actual reading on the pressure gauge corresponds to the calculated value.

When the flow through the sampler has been thus "matched" to the velocity of the gas flow in the stack, a particulate sampling can be taken on the filter. The sampling period is chosen such that it is long enough to obtain a sufficient sample for an accurate weight determination. Assuming the gas flow in the stack to remain at a constant temperature and velocity, the value obtained will be accurate with no adjustment of the control valve required.

Governmental authorities, however, often require that particulate emissions be measured at different locations across a stack. These locations often have different temperature and velocity readings. Such requires continual adjustment of the apparatus by the operator in order to maintain isokinetic flow. Also, the flow at a given point in a stack often varies and is not constant over the sampling period, such that inaccuracies in a reading inevitably occur.

Governmental authorities also require that the particulate emssions for a given reading be related to the particular volume of gas flow in which such emissions occur. Obtaining such a total volume requires an integration of the stack velocity over the period of time consumed during the test. This represents a further source of error, as will be appreciated.

Finally, manual adjustment of a sampler to achieve isokinetic conditions unavoidably incorporates operator error in measuring the several quantities required to make the determination and in adjusting the flow as required.

It is thus the principal object of the present invention to provide an isokinetic sampling apparatus of the type described that will be able automatically to compensate for varying gas temperatures and velocities in a given stack or other conduit in which particulate emissions are to be measured.

It is a further object of the present invention to provide such a sampler that will be able to measure the total volume of flow against which the particulate emissions obtained can be related.

It is a still further object of the present invention to provide a sampler of the type described that will minimize error and achieve increased accuracy in measuring particulate emissions.

SUMMARY OF THE INVENTION

The sampler of the present invention includes an inlet nozzle disposed at one end of a generally cylindrical sampling tube and is adapted for insertion into a stack or like conduit through which a gas is flowing. Means are provided automatically to read the temperature of the gas flowing in the stack. Means are further provided automatically to read velocity pressure across a Pitot tube mounted exteriorly of the nozzle and adapted for insertion into the stack with the nozzle.

A filter is disposed in the tube and suction pressure applying means are provided in communication with the downstream end of the tube. A flow measuring orifice is disposed in the tube and a control valve is provided to regulate the flow therethrough. Means are provided automatically to read the drop in pressure across the orifice, as well as the temperature of the gas flowing therethrough.

The apparatus includes means to calculate the required flow rate through the sampling tube for isokinetic sampling. Finally, means are provided automatically to adjust the control valve, thereby to adjust the flow rate through the sampler to achieve isokinetic flow conditions and to maintain the same during the sampling of a flow in a stack.

The subject matter which we regard as our invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 1 is a side view of a sampler in accordance with the present invention;

FIG. 2 is a perspective view of the filter housing;

DESCRIPTION OF THE PREFERRED EMBODIMENT

Figure 3:
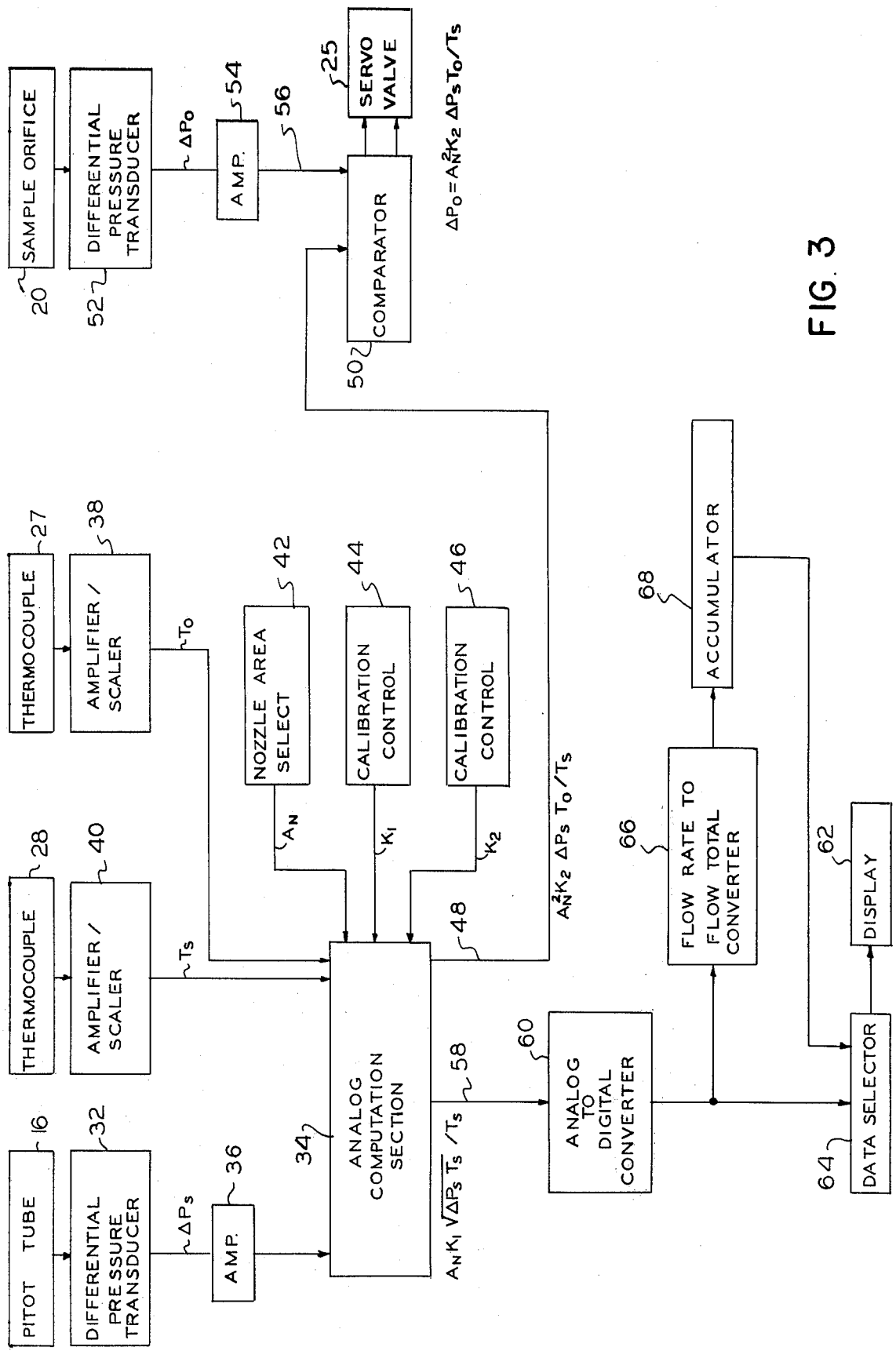
FIG. 3 is a block diagram of electronic circuitry for bringing about isokinetic flow conditions and providing output measurements.

Referring to the drawings and particularly to FIGS. 1 and 2, the sampler 10 of the present invention has a generally tubular body portion 11 and an inlet nozzle 12 bent to facilitate insertion into a stack or similar conduit through which a gas is flowing. A filter housing 13 is disposed intermediate the ends of the body portion and includes an upstream section 14 and a downstream section 15 hingedly connected together to facilitate access to a sheet of filter material 19 disposed therebetween. A Pitot tube 16 is attached to one side of the inlet nozzle 12 and has static pressure lines 17, 18 secured to the body as shown.

A flow measuring orifice meter 20 is disposed within the body portion 11, pressure connections 21, 22 being provided on both sides thereof for measuring the drop in pressure thereacross. A suction blower 23 is provided separate from the main body portion, being connected to the downstream end thereof by a length of flexible hose 24. A butterfly control valve 25 is disposed downstream of the orifice meter 20 for controlling the rate of flow through the sampler. A gear motor 26 is attached to the side of the sampler for actuating the valve.

A temperature measuring connection 27, suitably comprising a thermocouple, is provided downstream of the orifice meter 20 for measuring the temperature of the flow through the sampler.

A temperature sensing element 28, suitably comprising a thermocouple, is attached to the inlet nozzle 12 for measuring the temperature of the gas flowing in the stack.

Bracket 29 mounted upon the tubular body houses differential pressure transducers and, together with cabinet 30, houses electronic calculating circuitry for bringing about isokinetic flow conditions through control of valve 25. Cabinet 30 also includes measurement means for displaying the flow rate and flow of gas passing through the device.

For desired measurement conditions of isokinetic flow, the stack velocity $V_s'$ equals the nozzle velocity, $V_N$, of the sampler. The stack velocity is measured with a Pitot tube. For a Pitot tube measuring gas flow with the velocity pressure measured in inches of water, $$V_S = \sqrt{2gK\Delta P_S T_S/460}$$

wherein $V_S$ = velocity of gas in feet per second,
$g$ = acceleration of gravity in feet per second$^2$,
$K$ = a constant to convert feet of gas to inches of water,
$\Delta P_S$ = stack velocity pressure in inches of water, and
$T_S$ = temperature of stack gas in degrees Rankin.

Combining constants results in the following expression $$V_S' = K' \sqrt{\Delta P_S T_S}$$

wherein $V_S'$ = stack gas velocity in feet per minute,
$K'$ = a constant,
$\Delta P_S$ = stack velocity pressure in inches of water, and
$T_S$ = stack temperature in degrees Rankin.

For the sampling nozzle, $$Q_N = A_N V_N$$

or $$V_N = Q_N/A_N$$

wherein $Q_N$ = flow through the nozzle in cubic feet per minute,
$A_N$ = area of the nozzle in square feet, and
$V_N$ = velocity at the nozzle in feet per minute.

Since for isokinetic flow, the stack velocity must equal nozzle velocity, or $V_S' = V_N$, then $$K' \sqrt{\Delta P_S T_S} = Q_N/A_N$$

but $$Q_N = Q_O T_N/T_O$$

wherein $Q_O$ = flow through orifice 20 in cubic feet per minute,
$T_O$ = temperature of sample at orifice in degrees Rankin, and
$T_N$ = temperature of sample at nozzle in degrees Rankin.

Also $T_N = T_S$ because the nozzle takes the sample at the stack temperature. Therefore, $$K' \sqrt{\Delta P_S T_S} = \frac{Q_O T_S}{T_O A_N}$$

and $$Q_O = A_O V_O'$$

wherein $A_O$ = the area of the orifice 20 in square feet, and
$V_O'$ = velocity at the orifice in feet per minute.

Consequently, $$K' \sqrt{\Delta P_S T_S} = \frac{A_O V_O' T_S}{T_O A_N}$$

and:

$$V_O' = K'' \sqrt{2gK\Delta P_O T_O/460}$$

wherein $V_O'$ = velocity at the orifice 20 in feet per minute,
$K''$ = combined orifice coefficients,
$K$ = constant to convert feet of gas to inches of water,
$\Delta P_O$ = orifice pressure drop in inches of water, and
$T_O$ = temperature of the sample at orifice 20 in degrees Rankin.

Combining constants $$V_O' = K''' \sqrt{\Delta P_O T_O}$$

where $K'''$ is a constant.
Therefore, $$K' \sqrt{\Delta P_S T_S} = \frac{A_0 T_S}{A_N T_0} K''' \sqrt{\Delta P_0 T_0}$$

or $$K' A_N T_0 \sqrt{\Delta P_S T_S} = A_0 T_S K''' \sqrt{\Delta P_0 T_0}$$

Squaring both sides, $$(K' A_N T_0)^2 \Delta P_S T_S = (A_0 T_S K''')^2 \Delta P_0 T_0$$

Therefore, $$\Delta P_0 = \frac{K'^2 A_N^2 T_0^2 \Delta P_S T_S}{A_0^2 T_S^2 K'''^2 T_0}$$

Combining constants and $A_0^2$, which is constant for the given apparatus, $$\Delta P_0 = A_N^2 K_2 \Delta P_S T_0 / T_S \qquad (1)$$

where $K_2$ is a combined constant.

If the conditions of this equation are maintained, then isokinetic flow will be present which is the desired condition for measurement. The electronic circuitry as hereinafter described measures the quantities $T_S$, $\Delta P_S$ and $T_0$ on a continuous basis, and controls $\Delta P_0$ such that the equality of expression (1) is maintained.

As mentioned above, the flow through the nozzle in cubic feet per minute =

$$Q_N = A_N V_N$$

but $$V_N = V_S'$$

therefore $$Q_N = A_N K' \sqrt{\Delta P_S T_S}$$

To correct for standard temperature and pressure, the above quantity is multiplied by $T_A/T_S$, where $T_A$ is standard temperature. Assuming the standard temperature to be constant, then the flow through the nozzle in cubic feet per minute equals $$A_N K_1 \sqrt{\Delta P_S T_S / T_S} \qquad (2)$$

where $K_1$ is a combined constant. As hereinafter more fully described, electronic circuitry employed according to the present invention implements this expression to indicate the flow through the nozzle so that the user can ascertain the weight gain of particulate material collected relative to flow.

Referring to FIG. 3, comprising a block diagram of automatic control circuitry according to the present invention, differential pressure transducer 32, deriving its pressure reading from Pitot tube 16 via lines 17, 18, provides a first input $\Delta P_S$ to analog computation section 34 via preamplifier 36. Thermocouples 27 and 28 also provide inputs to analog computation section 34 by way of preamplifiers 38 and 40, respectively, which may be employed as scalers. Also, a nozzle area selection control 42 provides an input, $A_N$, indicative of the area of inlet nozzle 12, or such other nozzle as may be substituted therefor. Further inputs are supplied by calibration controls 44 and 46 which respectively supply constants $K_1$ and $K_2$ as heretofore referred to.

Computation section 34 provides a first output on lead 48 for comparison in comparator 50 with the differential pressure as measured by transducer 52 across orifice 20 and amplified by preamp 54. The analog output on lead 48 corresponds to the quantity $A_N^2 K_2 \Delta P_S T_0 / T_S$ while the analog value on output lead 56 of amplifier 54 is equivalent to $\Delta P_0$. When the output on lead 56 is the same as the output on lead 48, comparator 50 supplies no driving signal to servo controlled valve 25 since isokinetic conditions are established. In the event the output on lead 56 is not the same as the output on lead 48, comparator 50 drives servo control valve 25 in a direction for reestablishing isokinetic flow conditions. Thus, within the accuracy of the system, isokinetic conditions are automatically maintained.

A second output from analog computation section 34 is provided on lead 58, this second output comprising an analog value equivalent to the quantity $A_N K_1 \sqrt{\Delta P_S T_S / T_S}$ which corresponds to the standard flow rate of gas (through the nozzle). Lead 58 is connected as an input to analog to digital converter 60. Display unit 62 suitably comprises the conventional device for continuously displaying decimal digits wherein each digit is represented by a plurality of horizontal and vertical segmental light emitters which are selectively energized.

The output of converter 60 is also coupled to flow-rate-to-flow-total-converter 66, the output of which is applied to accumulator 68. Accumulator 68 in effect integrates the flow rate, with time, and provides the total flow as an additional input selectable by data selector 64 for display on display unit 62. Accumulator 68 can be manually reset at the start of each run.

Figure 4:
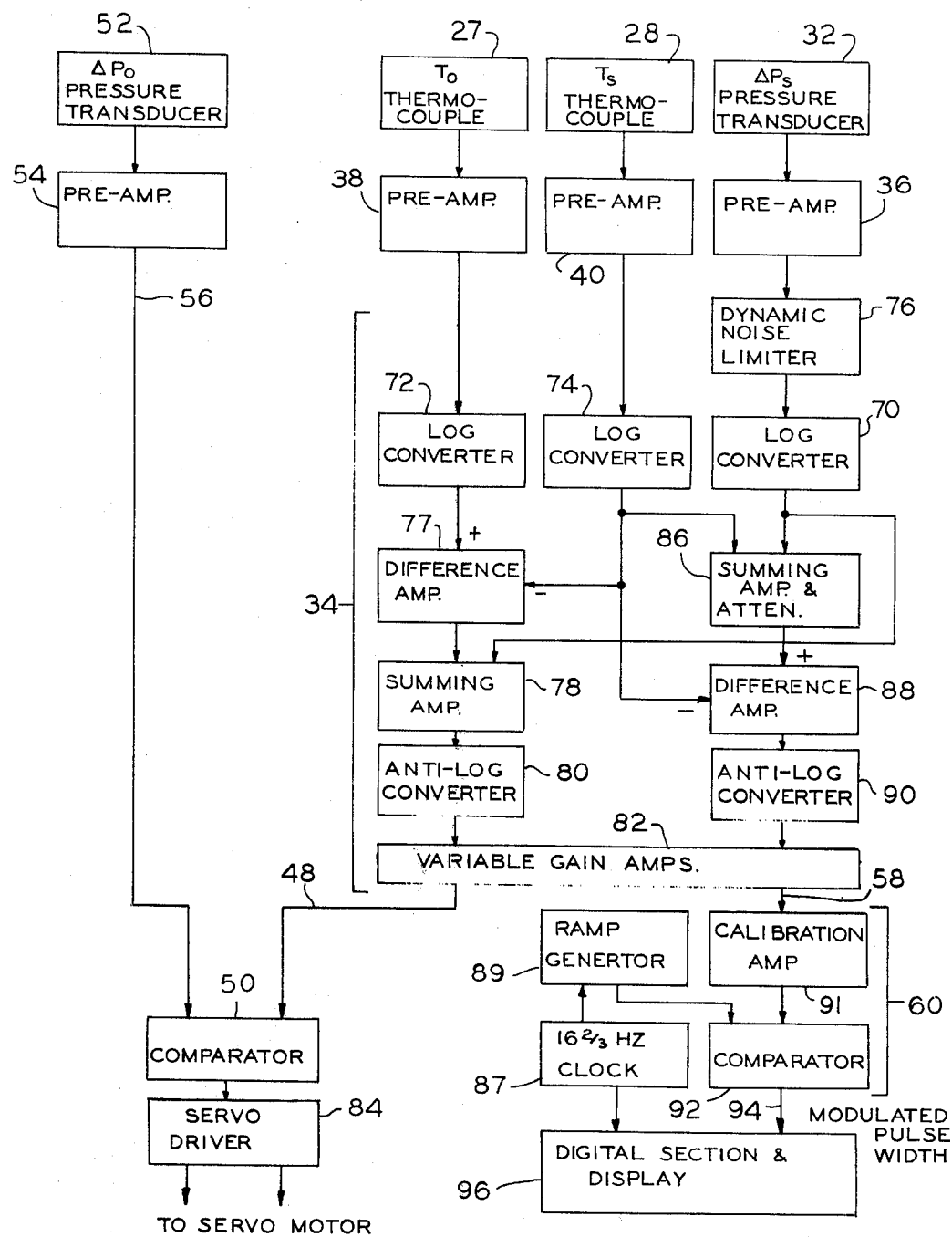
FIG. 4 is a more detailed block illustrating portions of the FIG. 3 circuitry.

Referring to FIG. 4, wherein like reference numerals refer to like elements, the analog computation section 34 is additionally illustrated. The outputs from amplifiers 36, 38 and 40 are respectively coupled to log converters 70, 72 and 74 which suitably comprise amplifiers providing an output proportional to the logarithm of the input supplied thereto. Dynamic noise limiter 76, hereinafter more fully described, is interposed between amplifier 36 and log converter 70.

The outputs of log converters 72 and 74 are respectively applied to positive and negative input terminals of difference amplifier 77, the output of which corresponds to the logarithm of $T_0$ minus the logarithm of $T_S$. As will be appreciated, the antilog of this difference would correspond to the ratio $T_0/T_S$ in expression (1).

The output of difference amplifier 77 together with the output of log converter 70 are coupled to summing amplifier 78, thereby accounting for the $\Delta P_S$ term in expression (1). This summed value is applied to antilog converter 80, the latter suitably comprising an amplifier having an antilogarithmic characteristic, whereby an output is produced which is proportional to $\Delta P_S T_0/T_S$, and this is applied to one portion of variable gain amplifier 82 controllable in gain in accordance with the term $A_N^2$. This multiplier value is ordinarily preset in accordance with the area of the inlet nozzle 12, or such other nozzle attachments as may be substituted therefore. The factor $K_2$ in expression (1) is suitably set into the device through adjustment of the gain of amplifier 54. Ordinarily, this factor will be initially preset in the device. The output of line 48 is coupled to comparator 50, as hereinbefore described, and the output of the comparator operates servo driver 84 as hereinafter more fully described.

The outputs of log converters 70 and 74 are also applied to summing amplifier and attenuator 86. The summing amplifier derives a signal proportional to the log of the product $\Delta P_S T_S$ in expression (2) while the attenuator, which is arranged to divide the output of the summing amplifier by two, provides a value proportional to the log of $\sqrt{\Delta P_S T_S}$. The output of circuit 86 and the output of log converter 74 are respectively coupled to the positive and negative inputs of difference amplifier 88 wherein the logarithm of $T_S$ is subtracted from the logarithm of $\sqrt{\Delta P_S T_S}$. The output of the difference amplifier is coupled via antilog converter 90 to another portion of variable gain amplifiers 82 wherein a multiplication proportional to $A_N$ is achieved. The portion of unit 82, receiving the output of converter 90, comprises an amplifier separate from the amplifier receiving the output of converter 80, but sharing a common gain control therewith. Antilog converter 90 suitably comprises an amplifier having antilogarithmic output characteristic. The factor $K_1$ in expression (2) is taken into account by appropriate gain adjustment of amplifier 91.

The amplifier portion of unit 82 receiving its input from converter 90 delivers its output on lead 58 to analog to digital converter 60 which here in part comprises clock generator 87, ramp generator 89, calibration amplifier 91, and comparator 92. The clock generator 87 comprises an oscillator having an output frequency of 16 hertz which triggers ramp generator 89 to produce a linear ramp waveform for each cycle of the clock generator. The output on lead 58 from the analog computation section is provided, via calibration amplifier 91 where exact adjustment for circuit accuracy can be made, to comparator 92. Comparator 92 produces output pulses starting with each ramp signal of ramp generator 89, i.e., once for each cycle of clock generator 87, and concluding when the linear ramp output of generator 89 reaches the analog value supplied from lead 58 via amplifier 91. It will be seen that the output of comparator 92 on lead 94 comprises a pulse waveform having a frequency of 16 hertz, and wherein the width of each pulse is proportional to the analog value on lead 58, i.e. $A_N K_1 \sqrt{\Delta P_S T_S / T_S}$. This pulse width modulated output on lead 94 is supplied to digital section and display unit 96 which is illustrated in more detailed form in FIG. 5.

Figure 5:
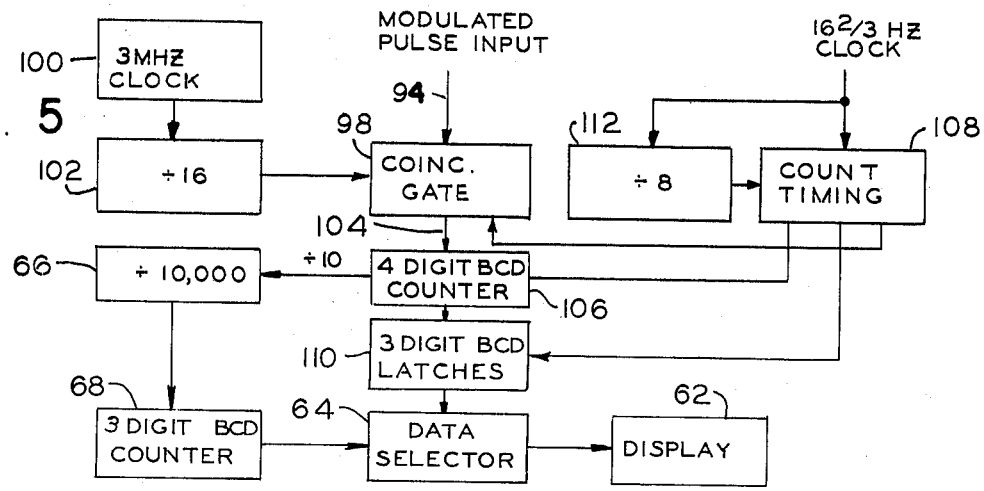
FIG. 5 is a detailed block diagram illustrating further portions of the FIG. 3 circuitry.

FIG. 5 illustrates in block diagram form additional circuitry for completing the analog to digital conversation, and for connection thereof to the data selector and display. The modulated pulse input on lead 94 is supplied to coincidence gate 98 which receives additional input from three megahertz clock generator 100 via a divide-by-sixteen circuit 102, the latter suitably comprising a counter. The output frequency from divide-by-sixteen circuit 102, as applied to coincidence gate 98, is then approximately 109 kilohertz. The calibration amplifier 91 (in FIG. 4) is set so that for a flow rate of 60 cubic feet per minute, count gate 98 provides 6,000 pulses on its output lead 104 for each modulated-pulse-width input on lead 94, i.e. 100 times the flow rate. The pulse output on lead 194 is counted by four digit BCD (binary coded decimal) counter 106, which may be reset after each count from count timing unit 108. The latter also receives the 16 hertz clock signal from clock generator 86 (in FIG. 4). The three higher order digits of the counter 106 are transferred to latches 110, before the counter 106 is reset, under the control of count timing unit 108.

Assuming the flow rate is 60 cubic feet per minute, then the number "600" will be transferred to latches 110 for display via data selector 64. Consequently, a decimal point is placed between the two zeros on the display. Naturally, the figure of 60 cubic feet per minute is given only by way of numerical example and the reading will change in accordance with the actual flow rate. In many cases, the flow rate changes rather frequently or rapidly, and it is desired that latches 110 retain the information for a somewhat longer period of time than would be dictated by a change at a frequency of 16 hertz. Consequently, the divide-by-eight circuit 112 is employed in conjunction with count timing unit 108 for resetting latches 110 approximately every one half second.

Accumulator 68 (from FIG. 3) suitably comprises a three digit BCD counter in FIG. 5 receiving its input from a divider 66 which divides its input by 10,000 and functions as the flow-rate-to-flow-total converter 66 of FIG. 3. (Divider 66 receives pulsations from lead 104 via a portion of counter 106 as hereinafter described.) During each counting interval of a pulse on lead 94, divider 66 couples to counter 68 the number of cubic feet flowing during that interval, with the assumption being made that no flow rate change takes place during an interval, or that such change is inconsequential relative to the overall calculation. The interval is the period of each cycle of 16 hertz provided by clock generator 87 (in FIG. 4), or approximately 0.06 seconds. Since the pulsation input on lead 94 is arranged to provide a count in cubic feet per minute, and it is desired to input a value to counter 68 indicative of the cubic feet for only a 0.06 second period, then the CFM value must be divided by 1,000 before being supplied as as input to counter 68. That is:

(cubic feet/min) × period in minutes = cubic feet or $$\frac{\text{(cubic feet/min)}/.06 \text{ sec}}{1000} = \text{cubic feet}$$

As hereinbefore indicated, the four digit counter 106 provides a count in CFM times 100, or the decimal point in the instance of counter 106 would be between the first two digits and last two digits in the counter. The number of output pulsations on lead 104 during an interval is CFM × 100. Consequently, the division of the pulses on lead 104 for inputting to counter 68 must be by 100,000 instead of 1,000. A first division of 10 is secured by obtaining the input of divider 66 from the output of the lowest order counter stage of counter 106, while divider 66 itself supplies a division ration of 10,000.

Considering again the specific example of a flow rate of 60 cubic feet per minute, wherein 6,000 pulses are produced on lead 104 during 0.06 second interval, it will be seen that only 6/100 of a pulse will be delivered to counter 68 by divider 66 during such interval. However, there are 1,000 such intervals during a minute and the result will be an accumulation of the correct value of 60 in counter 68 after the end of a minute, assuming the flow rate is constant. At the end of two minutes with the same constant flow rate, the number in counter 68 would be 120, and so on. As hereinbefore mentioned, the output from counter 68 is selectively displayed on display unit 62 by way of data selector 64.

The counter 68 may be manually reset at the start of every run, by means not shown.

In use, the apparatus continuously maintains isokinetic flow through the sampler, and the flow and flow rate are obtained from display 62. The material entrained by filter 19 is measured in the usual manner and is then related to the flow at the nozzle. The weight gain of filter material 19 is determined, corrected for the blank filter weight change and material washed from the sampler, and then calculation is made on the basis of grains per cubic foot at standard conditions, and total pounds per hour based on the emission velocity and area of the stack.

Figure 6:
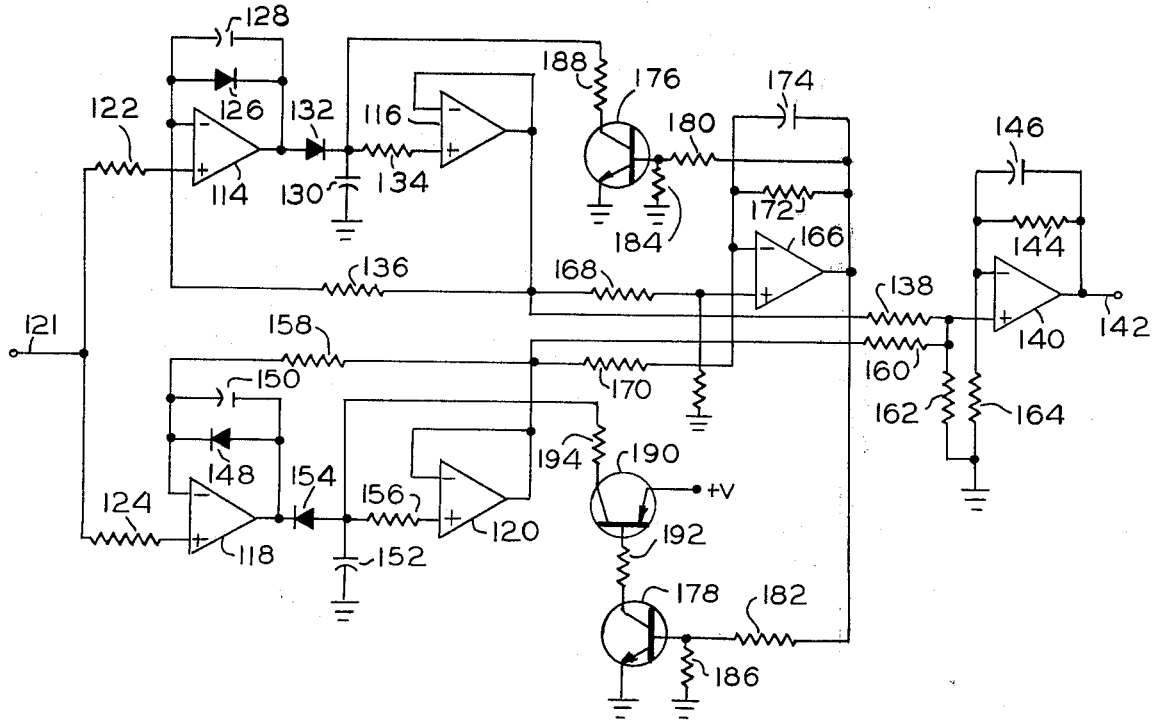
FIG. 6 is a schematic diagram of a dynamic noise limiter employed according to the present invention.

FIG. 6 illustrates in greater detail the dynamic noise limiter 76 of FIG. 4. At low values of differential pressure at transducer 32, the random noise generated in the transducer can introduce instability. Integrating this signal would eliminate the noise, but would sacrifice response time, and consequently the noise limiter provided discriminates between noise in the signal without substantial sacrifice of response time. Referring to FIG. 6, amplifiers 114 and 116 comprise a positive peak detector while amplifiers 118 and 120 comprise a negative peak detector or more accurately a positive valley detector. Input terminal 121 is coupled to the positive input terminals of amplifiers 114 and 118 through coupling resistors 122 and 124 respectively. The output of amplifier 114 is fed back to the negative input terminal thereof through a diode 126 shunted by a capacitor 128, wherein the anode of such diode is connected to the negative input terminal. Amplifier 114 drives integrating capacitor 130 through diode 132 having its anode connected to the output of amplifier 114 and its cathode connected to one terminal of capacitor 130 while the opposite terminal of capacitor 130 is grounded. The ungrounded terminal of the capacitor is further coupled via resistor 134 to the positive input terminal of voltage follower amplifier 116 having its output connected to its negative input. The output of amplifier 116 is also fed back to the negative input of amplifier 114 via feedback resistor 136.

The output of amplifier 116 is further coupled by way of resistor 138 to the positive input terminal of averaging amplifier 140 provided with a feedback circuit disposed between output terminal 142 which the amplifier drives, and the negative input terminal of the amplifier, such feedback circuit comprising resistor 144 shunted by capacitor 146. Resistors 162 and 164 return the positive and negative input terminals of amplifier 140 to ground.

The negative peak detector is connected in a similar manner wherein amplifier 118 is provided with a feedback circuit between its output terminal and negative input terminal, such feedback circuit comprising diode 148 shunted by capacitor 150. The anode of the diode is connected to the output of amplifier 118. The amplifier 118 further drives integrating capacitor 152 through diode 154, the anode of diode 154 being connected to one end of capacitor 152 while the remaining end thereof is grounded. The ungrounded end of capacitor 152 is further coupled to the positive input terminal of voltage follower amplifier 120 by means of resistor 156. A feedback resistor 158 is interposed between the output of amplifier 120 and the negative input of amplifier 118, and a coupling resistor 160 connects the output of amplifier 120 to the positive input terminal of amplifier 140.

As the input at terminal 121 becomes more positive, amplifier 114 charges capacitor 130 through diode 132, and capacitor 130 tends to retain the most positive input applied thereto. Thus, if the input at terminal 120 drops, diode 132 is back biased. Similarly, capacitor 152 tends to retain the least positive voltage applied thereto inasmuch as diode 154 is reversed in polarity in comparison to diode 132. Of course, the charges on capacitors 130 and 152 can change slowly. Since amplifiers 116 and 120 are connected as voltage followers, the voltages substantially retained on capacitors 130 and 152 are coupled to the input of averaging amplifier and hence the output thereof at terminal 142 will be the average of the inputs supplied at terminal 120. Thus, if the input at terminal 121 comprises the desired reading, plus random noise, the output at terminal 142 will represent the desired reading with the noise being filtered out.

The outputs at amplifiers 116 and 120 are also coupled respectively to positive and negative inputs of amplifier 166 through input resistors 168 and 170 respectively. Amplifier 166 is provided with a feedback circuit comprising resistor 172 shunted by capacitor 174 disposed between the output terminal of the amplifier and the negative input terminal. The output of amplifier 166 drives a pair of transistors 176 and 178 through coupling resistors 180 and 182 respectively interposed between the output of amplifier 166 and the base terminals of the said transistors. Resistors 184 and 186 return the transistor bases to ground while the emitter terminals thereof are grounded. The collector of transistor 176 is coupled to the undergrounded terminal of capacitor 130 via resistor 188. The collector of transistor 178 is coupled to the base of an inverting transistor 190 through resistor 192, with the emitter of transistor 190 being connected to a positive voltage and its collector being coupled to the underground terminal of capacitor 152 by means of resistor 194.

Transistors 176, 178 and 190 make up a feedback circuit which allows the peak and valley detectors to adjust rapidly to large changes in voltage at input terminal 120. Amplifier 166 is connected so that it provides an output representative of the difference between the output of the peak and valley detectors. If a sudden change occurs in the input at terminal 121, the output of either amplifier 116 or 120 will immediately follow it, according to the polarity of the change. The output of amplifier 166 causes normally nonconducting transistors 176, 178 and 190 to saturate, whereby the time constants associated with capacitors 130 and 152 are materially shortened allowing both capacitors to adjust rapidly to changes in input voltage. Then when the voltages at the outputs of amplifiers 116 and 120 again differ by only the noise component, the voltage at the output of amplifier 166 will return to near zero. Thus, the noise limiter can cancel random noise and still respond rapidly to large changes in input voltage.

In the foregoing circuit of FIG. 6, diodes 126 and 148 allow diodes 132 and 154 to operate in a precision manner whereby the stored values on capacitors 130 and 152 can be the desired peak values. The feedback diodes compensate for the voltage drop across the diodes driving the integrating capacitors. Feedback capacitors 128 and 150 are compensation capacitors which keep the respective amplifiers from oscillating.

Figure 7:
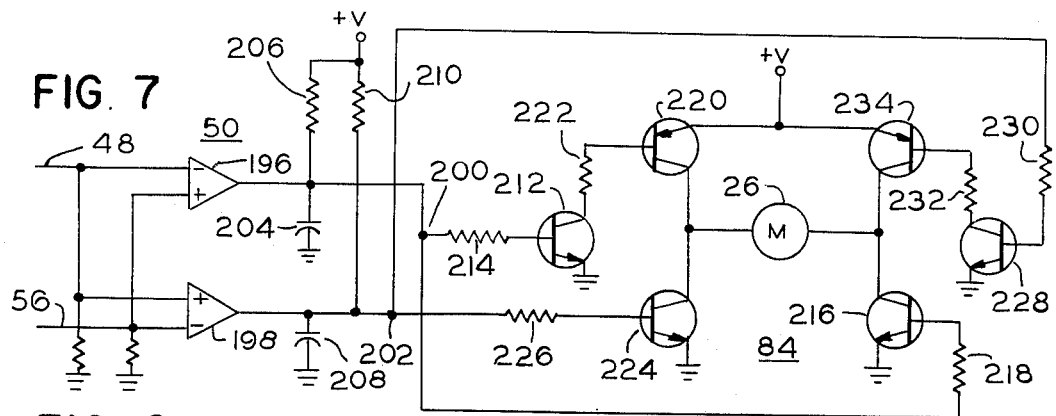
FIG. 7 is a schematic diagram of a comparator and servo driver employed according to the present invention.

Referring to FIG. 7, the comparator 50 and servo driver 84 (from FIG. 4) are more fully illustrated. Comparator 50 comprises a pair of amplifiers 196 and 198 having their input terminals differentially connected to leads 48 and 46 (in FIG. 4). Lead 48 from one of the commonly controlled amplifiers 82 is connected to the negative input terminal of amplifier 196 and the positive input terminal of amplifier 198. Lead 56 from amplifier 54 is connected to the positive input terminal of amplifier 196 and to the negative input terminal of amplifier 198. Then, when the voltage on lead 48 is more positive than the voltage on lead 56, the output terminal 200 of amplifier 196 will be at ground level while a voltage will be developed at output terminal 202 of amplifier 198. Conversely, when the voltage on lead 56 is greater than the voltage on lead 48, output terminal 202 will be at ground level and a voltage will be developed at output terminal 200. The capacitor 204 is disposed between output terminal 200 and ground and a resistor 206 is interposed between the output terminal and a positive voltage. Similarly, a capacitor 208 shunts terminal 202 to ground while a capacitor 210 connects the same point to a positive voltage. These integrating circuits adjust servo response.

Terminal 200 is coupled to the base of transistor 212 through resistor 214, and is also coupled to the base of transistor 216 by way of resistor 218. The collector of transistor 212 drives the base of a transistor 220 through resistor 222. Also, terminal 202 is connected to the base of transistor 224 via coupling resistor 226, and to the base of transistor 228 through coupling resistor 230. Resistor 232 connects the collector of transistor 228 to the base of transistor 234. Transistors 212, 216, 224 and 228 are of the NPN type and their emitter electrodes are grounded, while PNP transistors 220 and 234 have their emitters connected to a positive voltage.

The transistors 216, 220, 224 and 234 form a bridge circuit with servomotor 26 connected across the bridge from the collectors of transistors 220 and 224 to the collectors of transistors 216 and 234. When terminal 200 is positive, transistors 212, 216 and 220 are driven to saturation whereby current flows through the motor in a first direction from the collector of transistor 220 to the collector of transistor 216, driving motor 26 in a first direction. If, on the other hand, terminal 202 is positive, then transistors 224, 228 and 234 are driven to saturation whereby a current flows in a second direction through motor 26 from the collector of transistor 234 to the collector of transistor 224, driving motor 26 in the opposite direction. Motor 26 operates valve 25 in FIG. 1 in a direction for accomplishing isokinetic flow conditions. When the desired flow conditions are reached, whereby the inputs on leads 48 and 56 are substantially equal, motor 26 will be driven in neither direction. Lights may be connected to terminals 200 and 202, and if both are entirely out, stack flow below a measurable value of a negative flow is indicated.

While we have shown and described a preferred embodiment of our invention, it will be apparent to those skilled in the art that many changes and modifications may be made without departing from our invention in its broader aspects. We therefore intend the appended claims to cover all such changes and modifications as fall within the true spirit and scope of the invention.

We claim:

1. An isokinetic sampling apparatus for measuring particulate emissions in a gas flow, comprising:

tubular means for insertion in said gas flow for receiving a portion of said gas flow, filter means for collecting particulate matter, means for measuring velocity pressure in said gas flow as exerted by the flowing gas due to its kinetic energy, and temperature sensing means for sensing the temperature in said gas flow, means for measuring pressure drop in said tubular means, and temperature sensing means for sensing the temperature in said tubular means, suction pressure applying means attached to said tubular means for moving gas through said tubular means, means responsive to said means for measuring velocity pressure in said gas flow and to both said temperature sensing means for continuously calculating the pressure drop within said tubular means that would establish the volume rate of gas passing through said sampler as kinetically equivalent to the velocity of gas in said gas flow, and for calculating and providing a direct output reading indicative of gas flow in response to a measured pressure and temperature, and means responsive to said calculating means and to said means for measuring pressure drop in said tubular means for changing the flow in said tubular means as brought about by said suction pressure applying means until the measured pressure drop in said tubular means substantially equals the calculated value.

2. The apparatus according to claim 1 further including noise limiting means in a signal path receiving the velocity pressure in said gas flow, said noise limiting means comprising positive and negative signal peak detectors for receiving a common input, and an averaging means for receiving the outputs of said positive and negative signal peak detectors for providing an average output.

3. The apparatus according to claim 2 further including means responsive to a predetermined signal input excursion for temporarily lowering the time constant of said positive and negative peak detectors.

4. The apparatus according to claim 1 wherein said means responsive to said calculating means includes comparison means for comparing said measured pressure drop in said tubular means with the calculated value, and servo means comprising a servomotor operative for changing the flow in said tubular means, and a transistor bridge having said servomotor coupled thereacross and responsive to said comparison means for directing current through said servomotor in a direction for reducing the difference between the inputs of said comparison means.

5. An isokinetic sampling apparatus for measuring particulate emissions in a gas flow in a stack or like conduit comprising:

an inlet nozzle disposed at the forward end of said apparatus for insertion into said stack, Pitot tube means attached to said inlet nozzle for insertion into said stack with said nozzle, temperature sensing means attached to said inlet nozzle for measuring the temperature of the gas flowing in said stack, filter means disposed downstream of said inlet nozzle for collecting particulate matter from said gas, suction pressure applying means disposed at the downstream end of said apparatus for causing a flow of gas from said stack to pass into said inlet nozzle and thence through said apparatus, a flow measuring orifice disposed in said apparatus downstream from said filter means, temperature sensing means attached to said apparatus also downstream from said filter means for measuring the temperature of gas flow therethrough, and control means disposed in said apparatus for adjusting the volume rate of gas passing through said apparatus, means for continuously reading velocity pressure in said Pitot tube means, and means for continuously reading pressure drop across said flow measuring orifice, means responsive to said means for continuously reading the velocity pressure in said Pitot tube means and to said temperature sensing means for continuously calculating the pressure drop across said flow measuring orifice necessary for isokinetically matching flow rate through the sampler to gas flow in said stack, and means for automatically adjusting said control means for changing the volume rate of gas passing through said apparatus until the drop in pressure across said flow measuring orifice as measured by said means for continuously reading the same is substantially equal to said calculated pressure drop whereby said apparatus is capable of automatically and continuously isokinetically matching said gas flow in said stack while the same varies in temperature and velocity.

6. The apparatus according to claim 5 wherein said calculating means receives the temperature $T_S$ sensed at said nozzle, the temperature $T_O$ sensed for gas flowing through the apparatus, and the velocity pressure $\Delta P_S$ in said Pitot tube means, and continuously calculates the desired value of pressure drop $\Delta P_O$, across said flow measuring orifice according to the expression $\Delta P_O = A_N^2 K_2 \Delta P_S T_O / T_S$, wherein $A_N$ is the area of said nozzle and $K_2$ is a constant.

7. The apparatus according to claim 6 wherein said calculating means comprises:

means for converting values from said means for continuously reading velocity pressure in said Pitot tube means, from said temperature sensing means attached to said inlet Nozzle and from said temperature sensing means attached to said apparatus to logarithmic values, means for subtracting the logarithm corresponding to the temperature $T_S$ at the inlet nozzle from the logarithm corresponding to the temperature $T_O$ of gas flowing through the apparatus, means for adding the resultant to the logarithm corresponding to pressure drop $\Delta P_S$ in the Pitot tube means, and means for providing the antilog corresponding to the sum.

8. The apparatus according to claim 5 further provided with means for ascertaining the flow rate in said sampling apparatus.

9. The apparatus according to claim 8 wherein said means for ascertaining the flow rate comprises calculating means for determining said flow rate according to the expression $A_N K_1 \sqrt{\Delta P_S T_S / T_S}$, wherein $A_N$ is the area of the nozzle, $K_1$ is a constant, $\Delta P_S$ is said pressure drop in said Pitot tube means and $T_S$ is the temperature as sensed for gas flow in the stack.

10. the apparatus according to claim 8 further including means for integrating said flow rate to provide a total flow of gas in said apparatus.

11. The apparatus according to claim 9 wherein said calculating means for determining said flow rate comprises:

means for providing a signal proportional to the logarithm of the pressure drop $\Delta P_S$ in said Pitot tube means, and means for providing a signal proportional to the logarithm of the temperature $T_S$ of gas flow in the stack, means for adding the two logarithms, means for halving the resultant, means for subtracting the logarithm corresponding to the temperature $T_S$ of gas flow in the stack, and means for providing the antilog corresponding to the difference.

12. The apparatus according to claim 11 further including analog to digital converter means receiving as its input the output coupled from said means for providing the antilog, said analog to digital converter means comprising:

a ramp generator controlled for periodically supplying a ramp waveform, a comparator for receiving said input to the analog to digital converter means and for providing an output having a pulse length responsive to comparison of the ramp from said ramp generator with said input, a coincidence gate receiving the output of said comparator means while also receiving a stream of pulses, means for counting pulses gated by said coincidence gate, means for resetting said counting means between outputs from said comparator, and display means for providing a digital display of the count in said counting means.

13. The apparatus according to claim 12 further including integrating means for receiving the output of said coincidence gate, said integrating means comprising a counter for accumulating pulses in proportion to the output of said coincidence gate.

14. The apparatus according to claim 5 wherein said means for adjusting said control means for changing the rate of gas passing through said apparatus until the drop in pressure across said flow measuring orifice is substantially equal to said calculated pressure drop comprises means for comparing the measured value and the calculated value and servo means responsive to the output of the comparison means for operating said control means until the two inputs at said comparison means are substantially equal.

15. The apparatus according to claim 14 wherein said servo means comprises a servomotor for operating said control means and a transistor bridge circuit having said servomotor coupled thereacross and responsive to said comparison means for directing current through said servomotor in a direction for reducing the difference between the inputs of said comparison means.

* * * * *

UNITED STATES PATENT OFFICE
CERTIFICATE OF CORRECTION

PATENT NO. : 3,965,748
DATED : June 29, 1976
INVENTOR(S) : Richard W. Boubel et al It is certified that error appears in the above-identified patent and that said Letters Patent are hereby corrected as shown below:

Column 3, line 5, after "block" insert --diagram--.

Column 7, line 29, after "16" insert --2/3--.

Column 7, line 41, after "16" insert --2/3--.

Column 7, line 56, "109" should be --190--.

Column 7, line 64, after "16" insert --2/3--.

Column 8, line 12, after "16" insert --2/3--.

Column 8, line 29, after "16" insert --2/3--.

Column 8, line 54, "ration" should be --ratio--.

Column 8, line 58, after "during" insert --a--.

Column 10, line 32, "undergrounded" should be --ungrounded--.

Column 10, line 37, "underground" should be --ungrounded--.

Signed and Sealed this

Fourth Day of January 1977

[SEAL]

Attest:

RUTH C. MASON
*Attesting Officer*

C. MARSHALL DANN
*Commissioner of Patents and Trademarks*